United States Patent [19]

Morris et al.

[11] Patent Number: 4,952,586

[45] Date of Patent: Aug. 28, 1990

[54] EDROPHONIUM-ATROPINE COMPOSITION AND THERAPEUTIC USES THEREOF

[75] Inventors: Robert B. Morris, Mill Valley; Roy Cronnelly, Pacifica; Ronald Dean Miller, Greenbrae, all of Calif.

[73] Assignee: The Regents of the University of California, Berkeley, Calif.

[21] Appl. No.: 262,175

[22] Filed: Oct. 18, 1988

Related U.S. Application Data

[63] Continuation of Ser. No. 918,633, Oct. 14, 1986, abandoned, which is a continuation of Ser. No. 412,005, Aug. 27, 1982, abandoned.

[51] Int. Cl.$^5$ ............................................. A61K 31/44
[52] U.S. Cl. ..................................... 514/304; 514/821
[58] Field of Search ............................................. 514/304

[56] References Cited

PUBLICATIONS

L. Gyermek, *Int. J. Clin. Pharmacol.* 15 (1977), 356-362 (No. 8).
Morris, et al., Anesthesiology, vol. 54, No. 5, pp. 399-402 (May 1981).
Kopman, Anesthesiology, vol. 51, No. 2, pp. 139-142 (Aug. 1979).
Bevan, Anesthesia, vol. 34, pp. 614-619 (1979).
Azar, et al., Anesthesia and Analgesia, vol. 61, No. 2, pp. 167-168 (Feb. 1982).
Samra, et al., Anesthesiology, vol. 57, No. 3, p. A287 (Sep. 1982).
Foldes, et al., Anesthesiology, vol. 55, No. 3, p. A201 (Sep. 1981).
Cronnelly, et al., Br. J. Anaesth., vol. 54, pp. 183-194 (1982).
Ferguson, et al., Anesthesiology, vol. 53, No. 5, pp. 390-394 (Nov. 1980).
Katz, Anesthesiology, vol. 28, No. 2, pp. 327-336 (1967).
Remington's Pharmaceutical Sciences 16th ed., pp. 838-840, 850-853 (1980).
A. R. Hunter, "Tensilon: A New Anti-Curare Agent", *British Journal of Anaesthesia*, 24: 175-186 (1952).

*Primary Examiner*—Joseph A. Lipovsky
*Attorney, Agent, or Firm*—Majestic, Parsons, Siebert & Hsue

[57] ABSTRACT

A composition is provided which includes a balanced combination of an edrophonium component and an atropine component. A preferred embodiment has 0.5 mg of edrophonium chloride and 8 micrograms of atropine sulfate, with respect to patient weight. The inventive composition is useful to antagonize nondepolarizing blockade during medical treatment when muscle relaxation is no longer necessary, provides extremely rapid onset of action and results in minimal heart rate changes.

9 Claims, 2 Drawing Sheets

EDROPHONIUM-ATROPINE COMPOSITION AND THERAPEUTIC USES THEREOF

This is a continuation of application Ser. No. 918,633, filed Oct. 14, 1986, now abandoned, which is a continuation of Ser. No. 412,005 filed Aug. 27, 1982, now abandoned.

BACKGROUND OF THE INVENTION

1. Field of the Invention

The present invention generally relates to antagonism of neuromuscular blockade, and more particularly to antagonism of nondepolarizing blockade with a balanced combination of edrophonium and atropine.

2. Description of the Prior Art

Muscle relaxation agents are usefully administered to patients during a great variety of medical procedures, and may generally be characterized as either depolarizing agents or nondepolarizing agents. Nondepolarizing agents provide muscle relaxation for a longer duration than do depolarizing agents, and are generally curare-like drugs such as pancuronium, d-tubocurarine, metocurine, gallamine, vecuronium and atracurium.

Following a procedure where a nondepolarizing agent has been utilized, it is usually desirable that the neuromuscular blockade be antagonized when muscle relaxation is no longer necessary. Presently used antagonists are, for example, anti-cholinesterase drugs such as neostigmine (in combination with an anticholinergic) or pyridostigmine (in combination with an anticholinergic). These prior art compositions are occasionally associated with tachycardia, bradycardia and other dysrhythmias of atrial, nodal and ventricular origin. However, use of the anticholinesterase drugs as antagonists (without an anticholinergic) invariably leads to muscarinic effects such as bradycardia, or slowing of the heart rate, and hence a tendency for blood pressure to fall.

Edrophonium is a reversal inhibitor of acetylcholinesterase, but had been believed to have a brief duration of antagonism, thus allowing possible recurrence of neuromuscular blockade. It was recently reported that a controlled, two minute infusion of edrophonium (0.5 mg/kg) in combination with atropine (1.0 mg) during operative procedures with six patients appeared to provide adequate antagonism of neuromuscular blockade. However, thirty seconds following the start of the infusion the heart rate was observed to decrease, and thirty seconds later a tachycardia developed. Morris, et al., *Anesthesiology*, Vol. 54, pp. 399–402 (May, 1981).

SUMMARY OF THE INVENTION

It has been surprisingly discovered that a composition including edrophonium and atropine in particular, balanced amounts, when substantially simultaneously administered by rapid IV injection, provides extremely rapid onset of action (that is, timed from administration to peak antagonism) over an entire dose range which is significantly faster than the neostigmine or pyridostigmine composition presently used. Further, the substantially simultaneous administration of a composition in accordance with the present invention results in minimal changes in heart rate or mean arterial pressure (MAP). In addition, lower amounts of atropine are present in compositions of the subject invention than in the prior art compositions. Such lower doses are believed to result in fewer cardiac irregularities during therapeutic uses.

Accordingly, in one aspect of the present invention, a composition is provided which is useful for antagonizing nondepolarizing blockade in a patient of determined weight.

The composition comprises an edrophonium component and an atropine component with the components being in a carefully balanced weight ratio. The edrophonium component is in an amount sufficient to provide from about 0.3 to about 1 mg per kg of patient's weight. The atropine component is in an amount sufficient to provide from about 6 to about 10 microgram per kg of patient's weight. A preferred embodiment has 0.5 mg/kg of edrophonium chloride and 8 microgram/kg of atropine sulfate.

BEST MODE OF PRACTICING THE INVENTION

Figure 1:
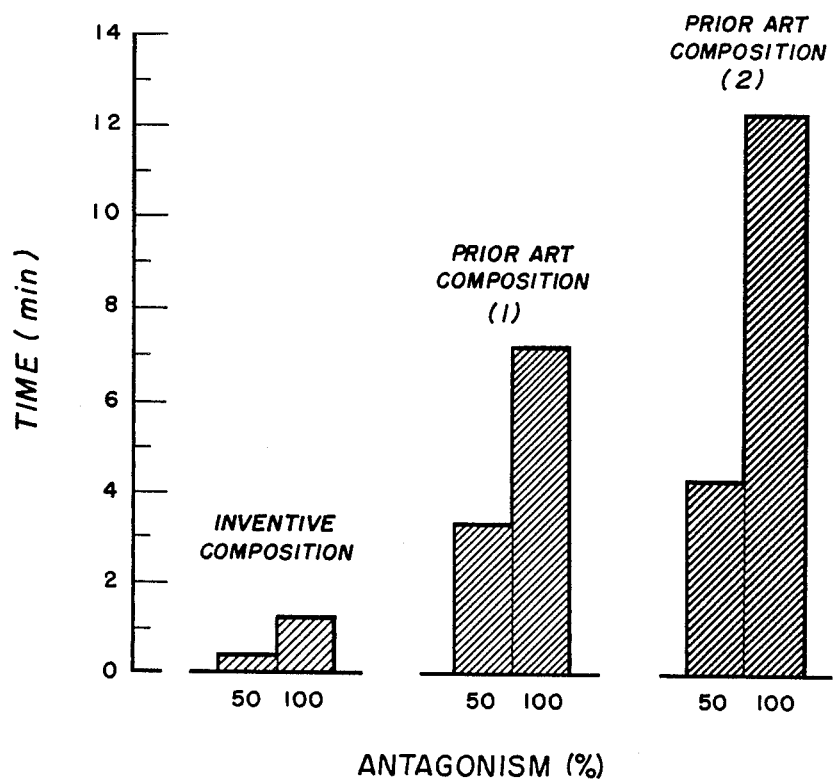
FIG. 1 illustrates the onset of action for a preferred embodiment in accordance with the present invention, a first prior art composition, and a second prior art composition; and, FIG. 2 illustrates plotted data for a prior art composition and a preferred embodiment of a composition in accordance with the subject invention. Data for both compositions are plotted as means ±S.E. for changes in heart rate as a percent of control.

A composition in accordance with the present invention includes an edrophonium component and an atropine component. Each component is commercially available.

The composition is preferably prepared in advance, ready for administration, as an aqueous solution in which the two essential components are solubilized, and may include other, pharmacologically suitable components, such as buffers, physiological salts, preservatives and the like.

For example, suitable pH adjustors, or buffers, include sodium citrate and citric acid; and, suitable preservatives include phenol andsodium sulfite.

The inventive composition may be prepared in advance of use, and packaged by means such as vials, prefilled syringes, or ampoules in appropriate volumes ready for administration.

A particularly preferred edrophonium component is edrophonium chloride. Preparation of several edrophonium derivatives (including edrophonium chloride and edrophonium bromide) is disclosed by U.S. Pat. No. 2,647,924, inventors Aeschlimann et al., assigned to Hoffmann-LaRoche Inc., issued Aug. 4, 1953.

A particularly preferred atropine component is atropine sulfate which, along with atropine and atropine hyperduric, has anticholinergic properties.

The edrophonium component in compositions of the subject invention are from about 0.3 to about 1 mg/kg, more preferably about 0.5 mg/kg which provides full antagonism for almost all adult patients in normal herapeutic uses. At amounts less than about 0.5 mg/kg an increasing number of adult patients will be without full antagonism. However, for pediatric patients it is believed the lower amounts (such as about 0.3 to about 0.5 mg) may be advisable. At about 0.5 mg/kg the edrophonium component is equiantagonistic (e.g. equivalent effectiveness) to neostigmine at the normal dose of about 0.043 mg/kg and to pyridostigmine at the normal dose of about 0.21 mg/kg.

The atropine component in compositions of the subject invention are from about 6 to about 10 microgram/kg, more preferably about 7 to 9 microgram/kg, most preferably about 8 microgram/kg. The inventive compositions include considerably less atropine than do many of the commonly used compositions For example, an optimal dose of atropine with 0.043 mg/kg neostigmine is 15 microgram/kg (about 1.1 mg for a 70 kg patient) by comparison with a preferred 0.56 mg (for a 70 kg patient) in the inventive composition.

The two essential components are carefully balanced in order that muscarinic effects (bradycardia) on one hand and anticholinergic (tachycardia) on the other hand are avoided. A weight ratio of the edrophonium component with respect to the atropine component should be in the range of about 50:1 to 100:1, more preferably 62.5:1 to 71.5:1. It should be understood that where the inventive composition is premixed and packaged by means such as ampoules, vials or the like, the composition's volume and the concentration of the two essential components therein may have been selected so as to provide sufficient of the two components with respect to an average patient's weight (or a normal range of weights).

For example, assuming an average patient weight of 70 kg, the inventive composition may be packaged in vials or ampoules (having about 5-15 ml volume) with about 35 mg edrophonium component and about 0.5 mg atropine component therein.

For more precisely adjusted administration to patients whose weight may be either within a normal range or outside a normal range, the composition may be, for example, packaged in prefilled syringes and a suitable or metered, volume of the inventive composition dispensed as appropriate.

Figure 2:
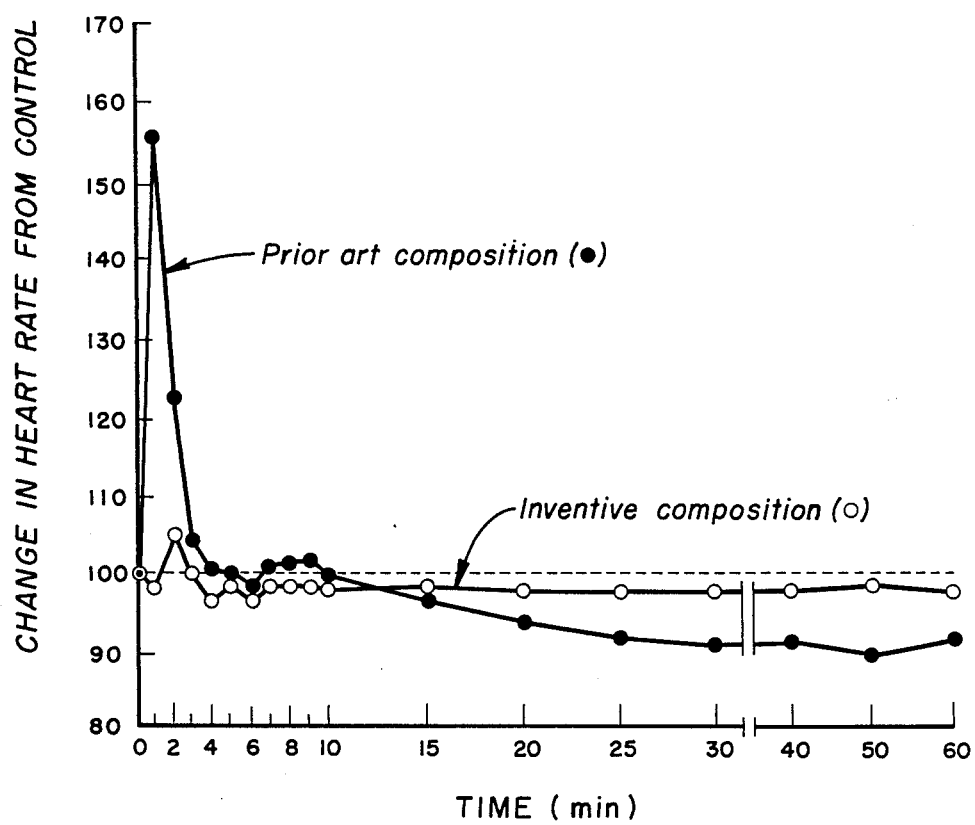

Compositions of the present invention result in very little heartbeat change in contrast to prior art compositions, as illustrated by FIG. 2. Heart rate data for the inventive composition illustrated by FIG. 2 was wherein edrophonium was 0.5 mg/kg and atropine was 0.7 microgram/kg, with the prior art composition having 0.043 mg/kg neostigmine and 15 microgram/kg atropine. As may be seen from FIG. 2, within the first two minutes following injection of the prior art composition, the heart rate rose to about 150% from control, whereas administration of the inventive composition during the same interval resulted in very little variation (about 105% from control). Further, from 15 minutes to one hour after administration of the inventive composition, heart rate variations were virtually nil, but heart rate dropped to about 90% from control for the prior art composition.

FIG. 1 illustrates the strikingly more rapid antagonism provided by the invention. The time to peak antagonism for an inventive composition (0.5 mg/kg edrophonium mixed with 7 microgram/kg atropine) is 0.8-2 minutes. By contrast, a first prior art composition (including neostigmine and atropine) required 7-11 minutes and a second prior art composition (including pyridostigmine and atropine) required 12-16 minutes.

The following experimental methods, materials and results are described for purposes of illustrating the present invention. However, other aspects, advantages and modifications within the scope of the invention will be apparent to those skilled in the art to which the invention pertains.

EXPERIMENTAL

Informed consent was obtained from surgical patients ASA (the American Society of Anesthesia) Class I and II. All patients had normal laboratory values for serum electrolytes, BUN, creatinine, SGOT and alkaline phosphatase About one hour following the oral administration of diazepam (10 mg), anesthesia was induced with thiopental (2-4 mg/kg) and maintained with nitrous oxide 60 percent inspired and halothane 0.4-0.7 percent end-tidal concentration as measured by mass spectrometer. Endotracheal intubation was accomplished without the use of muscle relaxants. Normal blood gases ($PaCO_2$ 35-40 mm Hg) and body temperatures (34°-36° C. esophageal) were maintained. Supramaximal squarewave pulses of 0.15 ms duration at 0.15 Hz were delivered to the ulnar nerve at the wrist through 27 gauge needle electrodes. The resultant force of thumb adduction was quantified with a Grass $FT_{10}$ force displacement transducer and recorded on a polygraph.

Example I, below, illustrates the antagonistic properties, onset of antagonism and duration of antagonism for compositions in accordance with the present invention and comparison compositions. Example II, below, illustrates blood pressure, heart rate and heart rhythm effect with compositions of the present invention (and comparison compositions).

EXAMPLE I

Methods

Neuromuscular blockade was achieved by administration of d-tubocurarine (dTC) as an intravenous bolus and then infused at a rate sufficient to maintain 90 percent depression of twitch tension. Adjustment of the infusion rate was required during the first 30 to 60 min. following which a stable level of neuromuscular blockade resulted, and the infusion was continued at this rate. After at least 20 min. of stable 90 percent blockade, twenty-six patients were divided into six groups, and each group treated with compositions having varying amounts of the edrophonium component (edrophonium chloride) but a constant amount of the atropine component (atropine sulfate), as illustrated by Table I, below.

TABLE I

| Group # | # of patients | Edrophonium (mg/kg) | Atropine (mg) |
|---|---|---|---|
| 1 | 3 | 0.03 | 0.5* |
| 2 | 5 | 0.06 | 0.5* |
| 3 | 5 | 0.125 | 0.5* |
| 4 | 5 | 0.25 | 0.5* |
| 5 | 5 | 0.50 | 0.5* |
| 6 | 3 | 1.00 | 0.5* |

(*About 7.1 microgram per kg, assuming an average patient weight of 70 kg.)

The compositions were administered by injection as a rapid IV bolus. Antagonism of twitch depression was determined as a percentage of the pre-existing 90 percent depression. (e.g. Control twitch height was 50 mm depressed to 5 mm by dTC. If peak twitch height after edrophonium was 30 mm, then the 5 mm twitch height remaining after the dTC was subtracted 30−5/50−5 or 56 percent of the dTC depressed twitch was antagonized by edrophonium.) In addition, the time required for twitch tension to increase to 50 percent of peak and to peak antagonism (onset of action) was measured, and the time required for twitch tension to decrease to 30 percent of peak effect (duration of action) was measured.

Data were analyzed by linear regression, analysis of variance and Chi Square Test. Differences were considered significant at P<0.05.

Results

The results obtained and discussed below are compared with previous work on neostigmine-atropine and pyridostigmine-atropine compositions administered under similar conditions, as reported by Miller, R. D. et al., *Anesthesiology*, Vol. 41, pp. 27-33 (1974).

The dose including edrophonium administered to Group (3) patients produced 50 percent antagonism of dTC depressed twitch $ED_{50}$. However, the dose response curve was not parallel to those of neostigmine and pyridostigmine. The dose including edrophonium which was administered to the Group (5) patients was equiantagonistic to compositions including neostigmine (0.043 mg/kg) or pyridostigmine (0.22 mg/kg). Since responses to the 1 mg/kg and 0.03 mg/kg doses did not fall on the linear portion (i.e. between 20 to 80 percent response) of the dose response curve, they were not included in the $ED_{50}$ determination. The dose including edrophonium administered to the Group (6) patients produced 100±0 percent antagonism (mean±S.E.), while the dose administered to the Group (1) patients produced 12±5 percent antagonism.

The onset of action (i.e. time from drug administration to peak antagonism) with doses including edrophonium was extremely rapid over the entire dose range, and was significantly faster than neostigmine (prior art composition 1) or pyridostigmine (prior art composition 2) at equiantagonistic doses. Table II, below, illustrates the onset data.

TABLE II

| Onset | Inventive Composition (including 0.5 mg/kg) | Prior Art Composition (1) (including 3 mg neostigmine) | Prior Art Composition (2) (including 15 mg pyridistigmine) |
|---|---|---|---|
| 50% | 0.4 ± 0.1 min | 3.2 ± 0.4 min | 4.0 ± 0.5 min |
| peak | 1.2 ± 0.2 min | 7.1 ± 0.6 min | 12.2 ± 1.8 min |

Dose dependent increase in the duration of antagonism occurred up to a dose including 0.125 mg/kg edrophonium above which no further increase could be produced. At equiantagonistic doses, the duration of edrophonium's antagonism did not differ from neostigmine, but duration for both was shorter than with pyridostigmine.

Example II

Methods

An additional 24 adult surgical patients, ASA Class I and II with normal preoperative electrocardiograms, were selected. Anesthesia was administered as described above. dTC (0.3 mg/kg) was administered IV and the response monitored by observing the train-of-four ($T_4$). When recovery of two of the four twitches in the $T_4$ occurred, the neuromuscular blockade was antagonized with either a composition in accordance with the present invention (having edrophonium chloride at 0.5 mg/kg and atropine sulfate at 7 microgram/kg referred to below as "Composition A") or with a prior art composition having neostigmine at 0.043 mg/kg mixed with its optimum dose of atropine (15 microgram/kg referred to below as "Composition D"). In addition, compositions including edrophonium and atropine, where the edrophonium component was 0.5 mg/kg but the atropine component was 15 (Composition "B") or 30 (Composition "C") microgram/kg, were utilized.

Measurements of blood pressure (using Dinamap blood pressure monitor), heart rate and rhythm (polygraph recording of EKG, lead II) were made at 1,2,3,4,5,6,7,8,9,10,15,20,25,30,40,50 and 60 min following antagonist administration.

The data of Table II, below, illustrates heart rate measurements over time expressed as the average percent of control heart rate.

TABLE III

| min | Comp. A Average % (1) | Comp. B Average % (2) | Comp. C Average % (3) | Comp. D Average % (4) |
|---|---|---|---|---|
| 1 | 98 | 145 | 148 | 70 |
| 2 | 105 | 132 | 151 | 156 |
| 3 | 100 | 129 | 146 | 104 |
| 4 | 96 | 129 | 144 | 99.9 |
| 5 | 98 | 129 | 144 | 98.7 |
| 6 | 96 | 130 | 143 | 97.7 |
| 7 | 98 | 131 | 141 | 100 |
| 8 | 98 | 128 | 140 | 101 |
| 9 | 98 | 128 | 139 | 101 |
| 10 | 98 | 127 | 138 | 98.6 |
| 15 | 97 | 121 | 134 | 96.6 |
| 20 | 97 | 118 | 133 | 93.3 |
| 25 | 97 | 114 | 132 | 91.1 |
| 30 | 97 | 101 | 130 | 90.4 |
| 40 | 97 | 100 | 127 | 90.9 |
| 50 | 98 | 102 | 123 | 89.1 |
| 60 | 97 | 100 | 123 | 91.3 |

(1) averaged from six patients with control heart rates of 77, 75, 88, 73, 77 and 101.
(2) averaged from seven patients with control heart rates of 70, 85, 90, 60, 64, 72 and 58.
(3) averaged from six patients with control heart rates of 72, 60, 72, 93, 67 and 72.
(4) averaged from seven patients with control heart rates of 93, 44, 58, 93, 66, 60 and 75.

Compared to neostigmine (0.043 mg/kg) and atropine (15 mg/kg), the simultaneous administration of edrophonium (0.5 mg/kg) and atropine (7μg/kg) resulted in minimal changes in heart rate or MAP.

Higher doses of atropine combined with edrophonium resulted in prolonged tachycardia and elevations in MAP.

What is claimed is:

1. A composition useful for antagonizing nondepolarizing neuromuscular blockade in a patient of determined weight by rapid intravenous unit dosage administration consisting essentially of:
    edrophonium in an amount of from about 21 to about 70 mg for each unit dosage of the composition, atropine in an amount of from about 0.42 to about 0.70 for mg each unit dosage of the composition, said edrophonium being in a weight ratio with respect to said atropine of about 50:1 to 100:1, said edrophonium and atropine being admixed.

2. The composition as in claim 1 wherein said edrophonium is substantially water soluble.

3. The composition as in claim 2 wherein said atropine is substantially water soluble.

4. The composition as in claim 3 wherein said composition is an aqueous solution, and said weight ratio is about 62.5:1 to 71.5:1.

5. The composition as in claim 1 or 4 herein said edrophonium is edrophonium chloride.

6. The composition as in claim 1 or 4 wherein said atropine is atropine sulfate.

7. The composition as in claim 1 wherein said edrophonium is edrophonium chloride in an amount of about 35 mg for each unit dosage, said atropine is atropine sulfate in an amount of about 0.49 to about 0.56 mg for each unit dosage, and said weight ratio is about 62.5:1 to 71.5:1.

8. The composition as in claim 7 wherein said edrophonium chloride and said atropine sulfate are solubilized in an aqueous solution.

9. A method for antagonizing nondepolarizing blockage in a patient of determined weight comprising the step of:

intravenously administering a dose consisting essentially of edrophonium sufficient to provide an amount from 0.3 to about 1 mg with respect to a kg of patient's weight, and atropine in an amount sufficient to provide from about 6 to about 10 micrograms with respect to a kg of patient's weight, the edrophonium and atropine being admixed in said dose with edrophonium being in a weight ratio with respect to the atropine of not less than about 50:1 and not greater than about 100:1, the administering of said dose of edrophonium and atropine being by a single, rapid injection.

* * * * *